US005294412A

United States Patent [19]

[11] Patent Number: 5,294,412

[45] Date of Patent: Mar. 15, 1994

Orlando

[54] STEAM AUTOCLAVE UNIT FOR DELIVERING STERILIZED MEDICAL WASTE TO A PORTABLE CARRIER

[75] Inventor: Joseph A. Orlando, Pleasantville, N.Y.

[73] Assignee: Health Care Waste Services Corp., Bronx, N.Y.

[21] Appl. No.: 954,163

[22] Filed: Sep. 30, 1992

Related U.S. Application Data

[62] Division of Ser. No. 678,445, Apr. 1, 1991, Pat. No. 5,186,397.

[51] Int. Cl.[5] .......................... A61L 2/06; B02C 19/12

[52] U.S. Cl. .......................................... 422/295; 422/1; 422/2; 241/23; 241/101.7; 241/606; 588/258

[58] Field of Search ................. 422/26, 295, 1, 2, 294; 241/23, 101.7, 606; 588/258

[56] References Cited

U.S. PATENT DOCUMENTS

| | | | |
|---|---|---|---|
| 4,552,720 | 11/1985 | Baker, Sr. et al. | 422/26 |
| 4,623,515 | 11/1986 | Frei et al. | 422/1 |
| 4,644,586 | 2/1987 | Padgett | 383/102 |
| 4,662,516 | 5/1987 | Baker, Sr. et al. | 206/363 |
| 5,003,892 | 4/1991 | Bricken | 110/46 |
| 5,084,250 | 1/1992 | Hall | 422/292 |
| 5,089,228 | 2/1992 | Meijer | 422/37 |
| 5,091,158 | 2/1992 | Drauscke et al. | 422/295 |
| 5,116,363 | 5/1992 | Romweber et al. | 34/22 |
| 5,119,994 | 6/1992 | Placzek | 241/17 |
| 5,124,125 | 6/1992 | Brent | 422/21 |
| 5,124,126 | 6/1992 | Ripp | 422/26 |
| 5,186,397 | 2/1993 | Orlando | 241/23 |

FOREIGN PATENT DOCUMENTS

| | | |
|---|---|---|
| 1146714 | 5/1983 | Canada . |

*Primary Examiner*—James C. Housel
*Assistant Examiner*—N. Bhat
*Attorney, Agent, or Firm*—Albert L. Gazzola; Carl P. Steinhauser

[57] ABSTRACT

A method of disposing of medical waste is disclosed wherein medical waste generated at a facility such as a hospital, clinic, and/or a doctor's office, after being bagged and sterilized, usually by a stem autoclave, is delivered to a mobile carrier having a shredder or similar device, for finely-dividing the sterilized waste which is then compacted and transferred to a storage area on the carrier where it can be commingled with sterilized shredded medical waste obtained from other facilities having been processed in like manner, before being transported to a sanitary disposal site.

9 Claims, 8 Drawing Sheets

STEAM AUTOCLAVE UNIT FOR DELIVERING STERILIZED MEDICAL WASTE TO A PORTABLE CARRIER

This is a division of copending application Ser. No. 07/678,445 filed on Apr. 1, 1991, now U.S. Pat. No. 5,186,397.

FIELD OF THE INVENTION

This invention relates to a method of collecting and disposing of autoclaved medical waste in a compact efficient and environmentally acceptable manner, and to a mobile device for processing, transporting and disposing of such medical waste.

BACKGROUND OF THE INVENTION

The disposal of medical waste has, heretofore, been an expensive, time-consuming, hazardous and labor intensive problem. Because medical waste may, and often does, contain highly infectious materials, before disposal sterilization is, and has been encouraged. Moreover, government regulations strictly control medical waste from collection to disposal. Severe penalties apply if the regulations are not adhered to. A manifest or record must be kept of each lot or batch of medical waste from collection to disposal, by law. Only certified licensed medical waste haulers are authorized to collect medical waste from medical facilities.

Solid medical waste includes solid, semi-solid and liquid material but does not include domestic sewage materials, as prescribed by law. It includes, for instance, waste from diagnosis and treatment of humans and animals, and in the production and testing of biologicals; cultures and stock of infectious agents and biologicals; waste from the production of biologicals, discarded virus cultures and vaccines and all the glassware and devices used in the foregoing. Human and animal wastes including tissues, organs, body fluids, etc., removed during surgery, research or autopsy, for instance, and all contaminated material such as dressings, bed linen, towels, bags, etc., associated therewith. It includes whole animal carcasses, body parts and bedding of infected animals.

Facilities generating medical waste, e.g., hospitals, clinics, and/or doctors' offices, have devices for sterilizing materials and instruments before use. Most such facilities have a steam autoclave so that the waste which is contained in red leak-proof bags, simply can be placed in the autoclave for sterilization, and the bags are then removed and placed in a waste receptacle such as a barrel or can, or in cardboard boxes, for instance, and picked up by a certified medical waste hauler for disposal.

In practice, for maximum bulk reduction, the medical facility bags and boxes its medical waste, in a cardboard box, for instance, for pick-up by the certified hauler. If the waste is autoclaved (sterilized) the hauler trucks it to a shredding facility and after shredding he loads another truck with the shredded waste, for eventual disposal. Thus, the hauler must load one truck with the sterilized medical waste, drive to a shredder facility, unload the truck, shred the waste, load it onto a second truck and finally dispose of it. Should the medical waste from a facility not be sterilized, the certified hauler must either dispose of it by incineration, an expensive procedure, or he may autoclave the bagged waste and process as above.

PRIOR ART

The pertinent prior art known to Applicant includes U.S. Pat. Nos. 3,189,286 and 3,192,853, both issued to James E. O'Connor which disclose an apparatus for destroying, disintegrating and disposing of classified documents. Classified documents to be destroyed are placed in locked wheel bins which can be moved into a mobile unit having a shredder device which can receive, and finely divide the classified documents. The shredded documents accumulate in the mobile unit and are disposed of in the customary manner. O'conner's device has a separate engine and does not solve the problem of processing regulated and unregulated medical wastes.

U.S. Pat. No. 3,589,276 to Swallart describes a destruction device for hospital use for destroying glass, plastic, paper and metallic articles by grinding and heating. There is not the slightest hint of the present described mobile unit for the shredding, compacting, containing and disposal of regulated medical waste, as dèscribed hereinafter.

U.S. Pat. No. 4,009,838 to Tashman also appears of interest because it discloses a portable solid waste shredder for shredding of wet or dry trash, glass, metal cans, cartons, wood, cardboard and synthetic plastics. The shredder device comprises oppositely rotating rotary shredding jaws and may be used in combination with a compactor by providing a discharge opening for the shredded waste at a position relative to an opening in the site of a compactor directing the shredded waste materials into the compactor to be compacted and baled along with waste materials directly fed into the compactor. Tashman has no concern for the disposition of regulated and unregulated medical waste and furthermore does not even hint at a highway useable unit such as presently described and claimed.

Also of interest is U.S. Pat. No. 4,860,958 to Yerman, which discloses a plastic syringe destruction device employing a cylinder and piston compactor unit together with heat to thermally smash plastic syringes into a compacted mass or slug. During compaction, the syringes are heated to temperatures between 100° C. and 200° C. to melt and sterilize the syringes. This patent discloses only a heating and compacting unit, it has no shredder and does not disclose highway mobility.

U.S. Pat. No. 3,956,981 to Pitt discloses a device for comminuting refuse into smaller particles which are blended to form an extrudable mass which is extruded through a die to form high-density, low-volume shapes suitable for burying in a landfill U.S. Pat. No. 4,961,539 to Deem discloses a heavy duty shredder, mounted on a truck frame, or chassis, for reducing solid wood to chips and a storage container for the chipped wood. The shredder is driven by the vehicle propulsion system. It has no utility for processing medical waste. Deem does not disclose or hint at solving the problem of shredding sterilized medical wastes in a compact, efficient and environmentally acceptable manner as presently described.

No other prior art known to Applicant describes a simple, effective system for the disposal of medical waste and the problems solved thereby as presently described.

SUMMARY OF THE INVENTION

The present invention makes available a mobile highway useable truck equipped with shredding means, compacting means and containing a storage area, whereby sterilized medical regulated waste is converted to shredded unregulated medical waste, compacted and contained on said truck for eventual disposal in a sanitary landfill. Only one truck and one operator is required in the practice of this invention, from the point of pick-up to disposal, even with multiple pickups from many facilities.

At the outset, the terms "regulated" and "unregulated" medical waste are defined as follows:

"Regulated Medical Waste" is either sterilized or unsterilized medical waste generated by a medical facility such as a hospital, clinic, and/or doctor's office which may include, for instance, blood-stained bandages, dressings, and the like, soiled linens or garments which may be urine-soaked or carry human feces, syringes, hypodermic needles, instruments being discarded, and any instrumentality contaminated by contact with diseased patients. Regulated waste cannot be intimately commingled with other such wastes, by law.

"Unregulated Medical Waste" is sterilized medical waste as described above which after sterilization, is shredded, or finely-divided into an amorphous mass. Such medical waste can be advantageously intimately commingled with amorphous masses of sterilized shredded medical waste from other facilities or even with ordinary garbage.

Accordingly, it is an object of this invention to facilitate the acquisition of regulated medical waste and convert it to unregulated medical waste from several medical facilities before disposal at a sanitary waste disposal site.

Another object of this invention is the conversion of regulated medical waste to unregulated medical waste in a unit mounted on a highway useable mobile carrier for disposal at a sanitary waste disposal site.

A further object of this invention is to collect, in a mobile carrier, regulated medical waste of several medical facilities, converting the regulated medical waste from each medical facility to unregulated medical waste, and combining the wastes for disposal at a waste disposal facility, all on one vehicle.

Another object of the invention is to provide a mobile carrier for medical waste capable of converting regulated medical waste to unregulated medical waste requiring a minimum of human handling and effort.

Yet another object of this invention is to provide a mobile carrier for medical waste requiring no human contact while converting the regulated medical waste to unregulated medical waste and storing same.

A further object of the invention is to provide a mobile carrier for medical waste wherein medical wastes from numerous facilities are intimately commingled after being .converted to unregulated medical waste.

Yet another object of the invention is to provide a mobile carrier for medical waste which allows the operator to collect the waste from a medical facility, convert it to unregulated medical waste, and disposing the waste at a sanitary waste disposal site simply by manipulating controls on the mobile carrier.

These and further objects of the invention will appear as the specification progresses.

In accordance with the invention a mobile carrier, such as a truck, is provided with a shredding device at one end for receiving regulated medical waste from a medical facility. This medical waste obtained in a manner about to be described, from a sterilization unit at the medical facility preferably positioned or located on a loading platform, is fed into the shredding device on the truck where the waste is reduced to a finely-divided amorphous mass. It is then compacted and moved into a storage area on the same truck. Since it is now unregulated medical waste, it may be mixed on this same truck with similarly treated wastes (unregulated) from other facilities and finally the collected unregulated medical wastes are disposed of in a suitable sanitary landfill, for instance. All this may be accomplished in one vehicle and with one operator.

In a preferred embodiment of the invention, the red bags of medical waste from a medical facility are sterilized by placing them in a basket in a steam autoclave. Steam autoclaves are conventional in medical facilities for sterilizing instruments and the like, and thus can be used for sterilizing medical waste. However, other forms of sterilization may be used such as ultra-violet radiation, ionizing radiation, or even microwave radiation. Therefore, the invention is not limited to the use of steam sterilization alone.

After sterilization the basket containing bags of sterilized medical waste is lifted out of the autoclave and emptied into a waste receptacle for delivery into the shredder on the mobile carrier. The basket sterilization is preferably entirely automated.

The shredded or finely-divided mass of medical waste is pushed by a piston in a cylinder connected to the output of the shredder to move and compact the shredded mass into a storage area of the truck. The shredder and piston compactor are conveniently driven by the truck transmission system by a power take-off from the main drive-shaft of the truck controlled by the operator, as known in the art.

After the operator has completed all pick-ups, he can then drive the truck to a sanitary waste disposal site where he can tip or elevate the body of the storage area of the truck from the chassis as known in the art allowing the contents to be emptied out into the waste-disposal site.

The mobile carrier may also be provided with a side door for receiving ordinary garbage should its storage area not be completely filled. This is made possible because unregulated medical waste may be legally commingled with ordinary garbage. The combined wastes are then disposed of at a disposal site.

The invention will be described in more detail in connection with specific embodiments thereof shown in the accompanying drawing. The invention is, however, not limited to what is shown in those embodiments, but is defined solely by the claims following this specification.

DETAILED DESCRIPTION OF THE DRAWINGS

Figure 1:
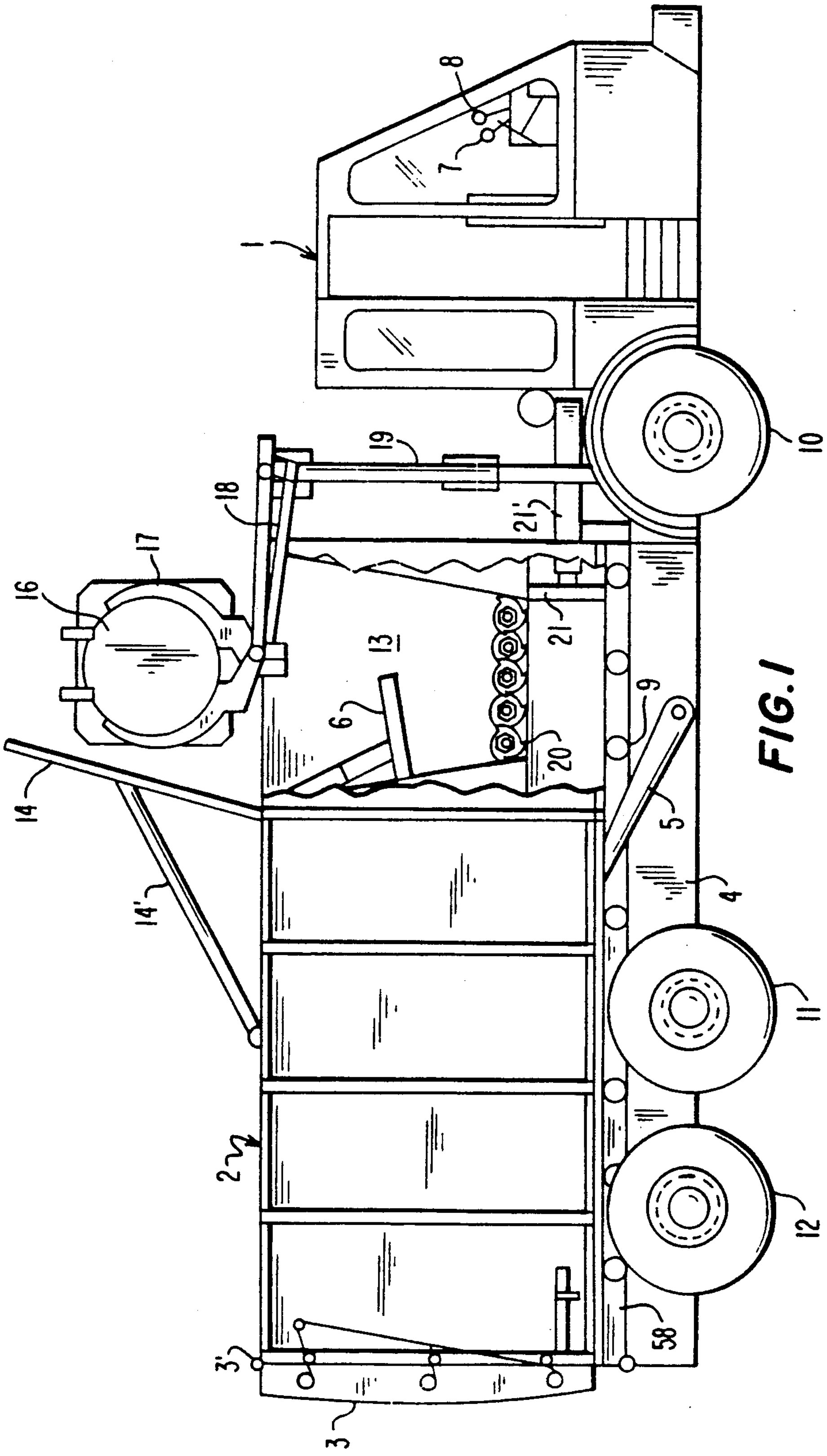
FIG. 1 is a side view in elevation and partly in section, of a mobile carrier according to the invention.
Figure 2:
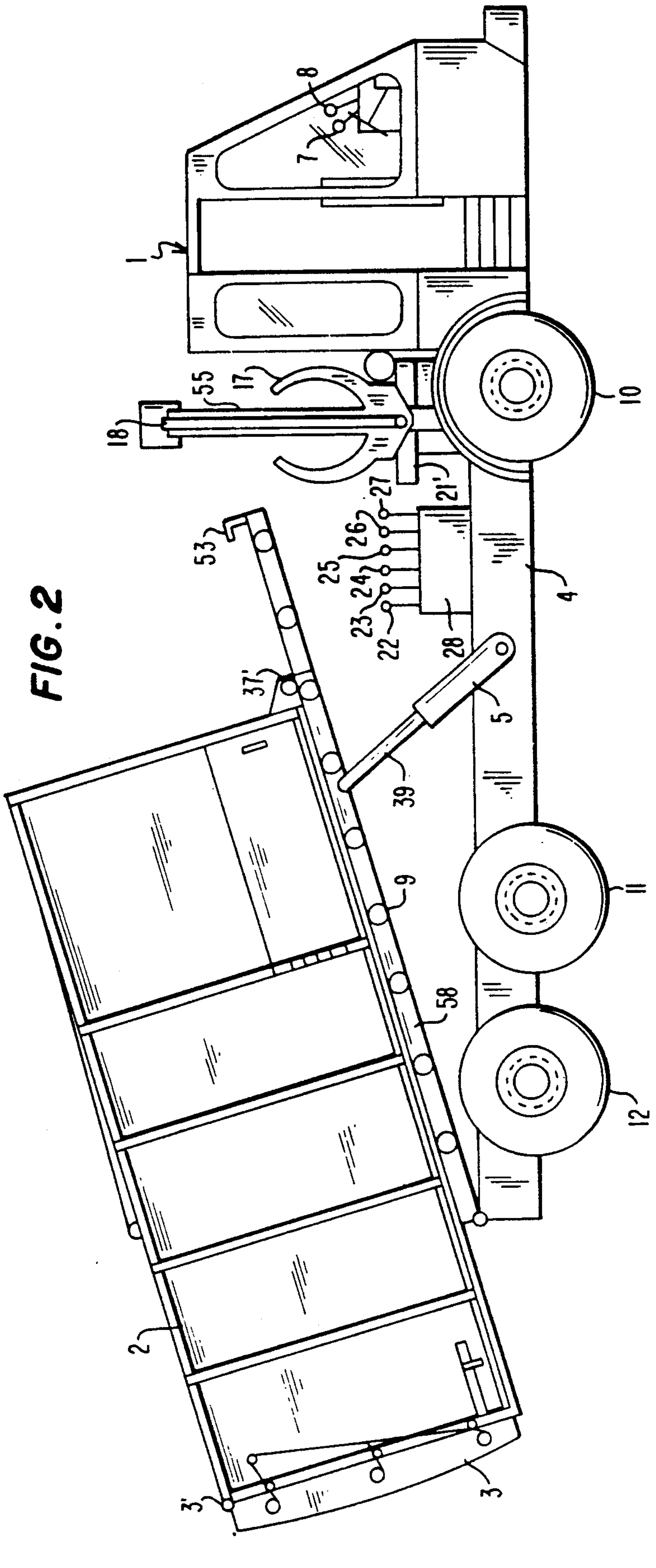
FIG. 2 is a side view in elevation of the mobile carrier of FIG. 1 shown in a raised position prior to emptying.
Figure 4:
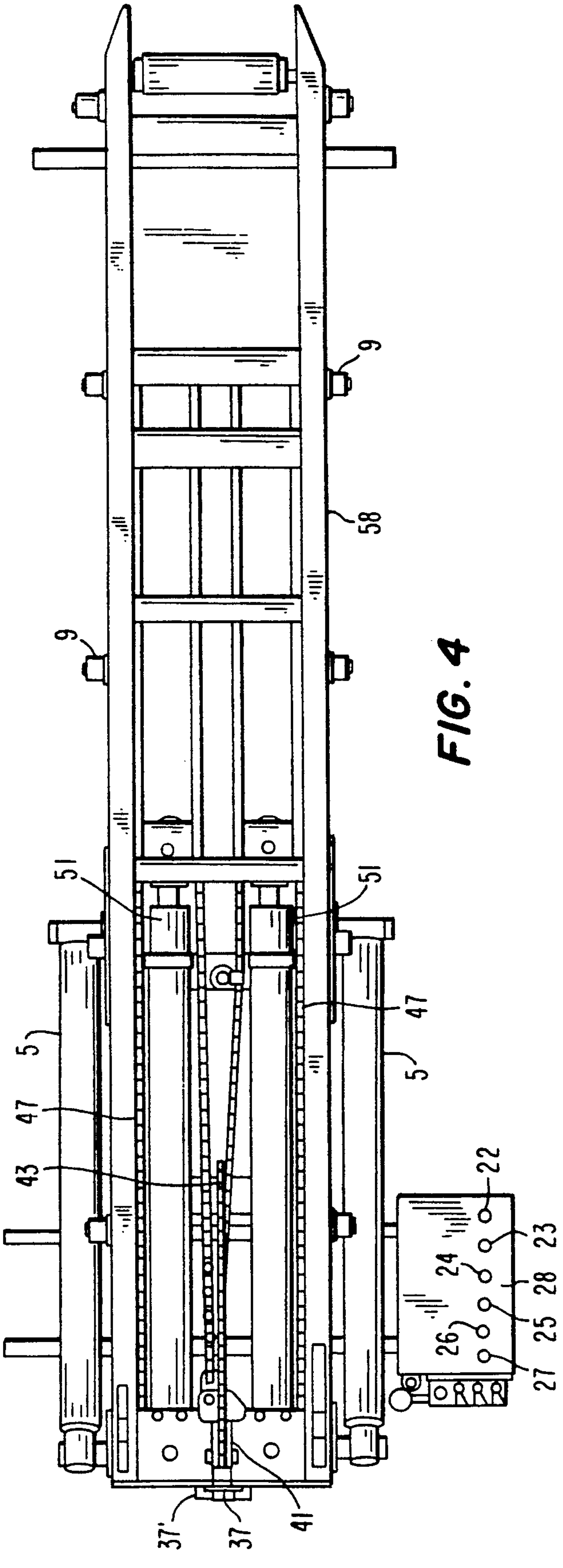
FIG. 4 is a plan view of the device mechanism for loading and unloading the carrier.

Referring to FIG. 1 which shows a mobile carrier having a chassis 4, cab 1, wheels 10, 11 and 12 and operating levers 7 and 8. Mounted on the carrier is a body storage area 2, having a rear door 3 with hinge 3$^1$, a body stop 53 and rollers 37 and 37$^1$ (FIG. 2). Storage area 2 rests on chassis 4 which is equipped with rollers 9 to permit the storage area 2 to move forward and backward on guide rail 58. A hydraulic lift cylinder 5 and piston 51 controlled by lever 8 in cab 1, which delivers power from the driving motor (not shown) activating cylinder 5 to lift storage area 2 which rolls to the rear along rollers 9 as shown in FIG. 2. A second lever 7 in the cab 1 operates the cable heave piston 55. (FIG. 4). These levers are a take-off from control box manifold 29 (FIG. 5) and may also be located on the manifold.

Figure 6:
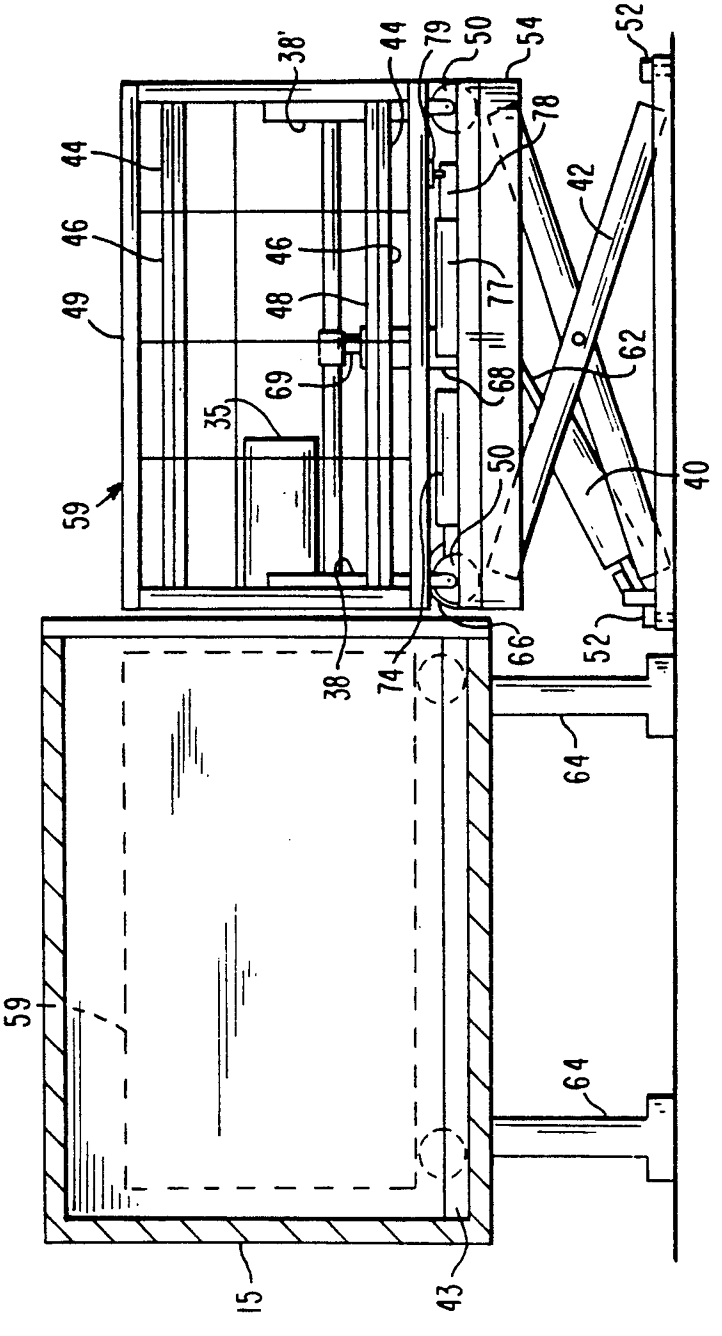
FIG. 6 is a side view partially in section of a autoclave unit preferably for use with the carrier.
Figure 7:
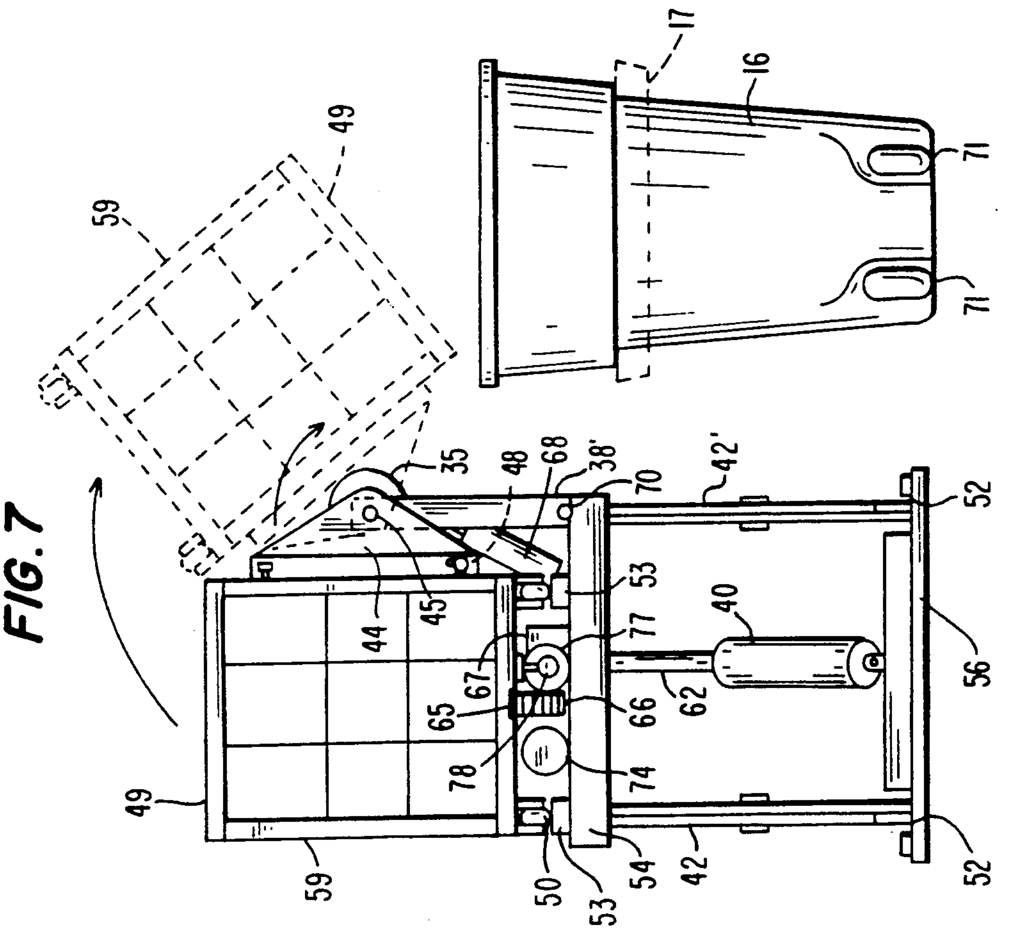
FIG. 7 is front plan view of the autoclave unit with a basket for medical waste being emptied into a receptacle.

The waste disposal unit in FIG. 1 includes a shredder bin 13, wherein the rotating shredder jaws 20 shred the medical waste to a finely divided mass. The waste is deposited into the shredder bin 13 through a hinged cover opening 14, from a receptacle 16 which receives the waste from an autoclave (FIGS. 6 and 7). The hinged cover is operated by hydraulic arm 14$^1$. Receptacle 16 is grasped by collar 17 and arm 18, lifted and pivoted depositing the waste into bin 13. An anti-coning device 6 presses down on the waste in bin 13 to insure total feed into shredder jaws 20. Collar 17 is actuated by a crank arm 18 driven by the truck motor (not shown) through a shaft 19. After shredding, the medical waste is compacted and moved into the storage area 2 by a hydraulically driven piston 21 in cylinder 21$^1$, also driven by the truck motor in a manner hereinafter described. The shredded waste is stored and further compacted in said storage area container 2 for eventual disposal An operator can operate all the foregoing without difficulty.

Figure 3:
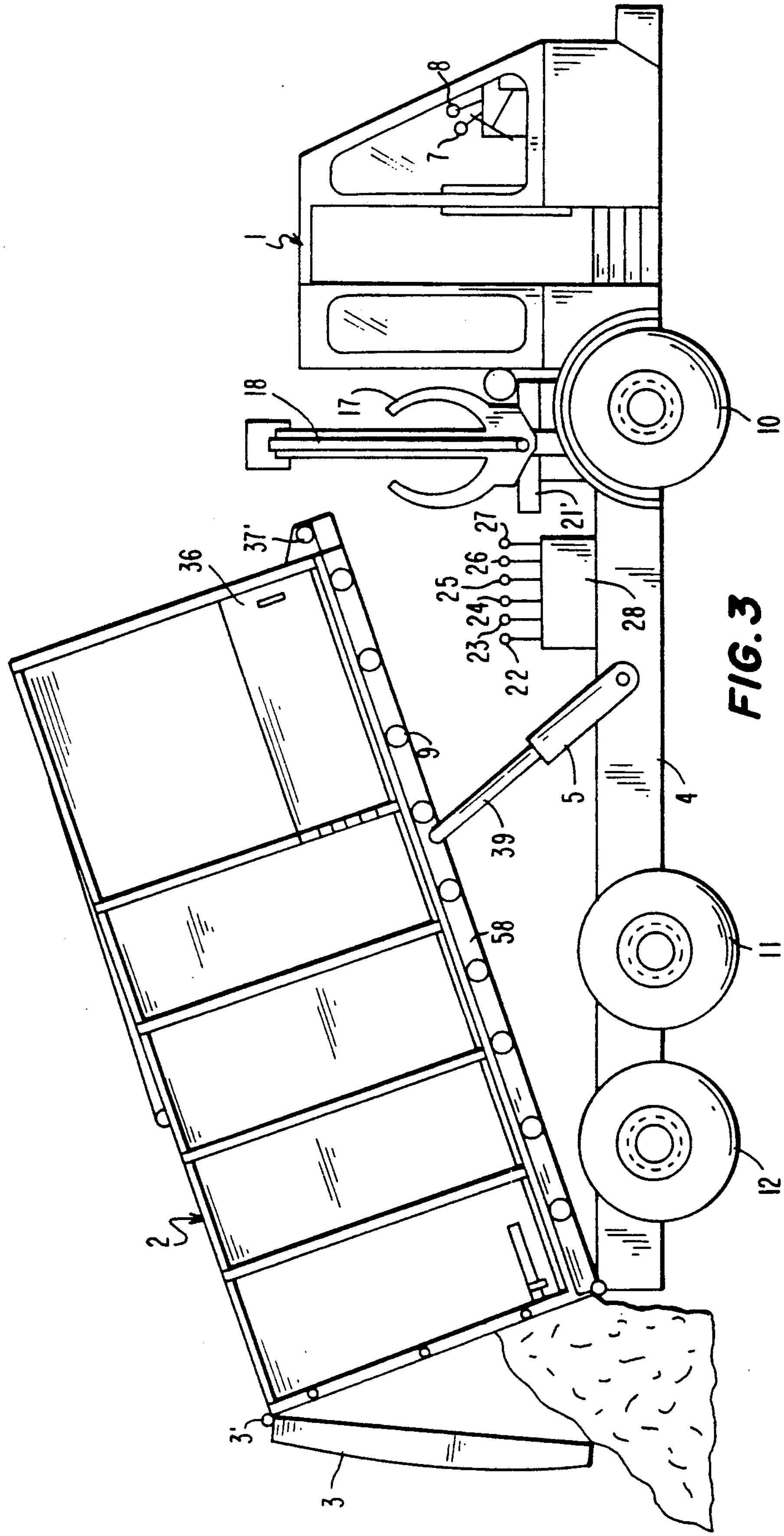
FIG. 3 is a side view in elevation of the carrier being emptied.

FIG. 3 also shows a hinged door 36 which may be opened by the operator to deposit ordinary garbage in order to fill the container 2 for final disposal of the contained waste.

Figure 5:
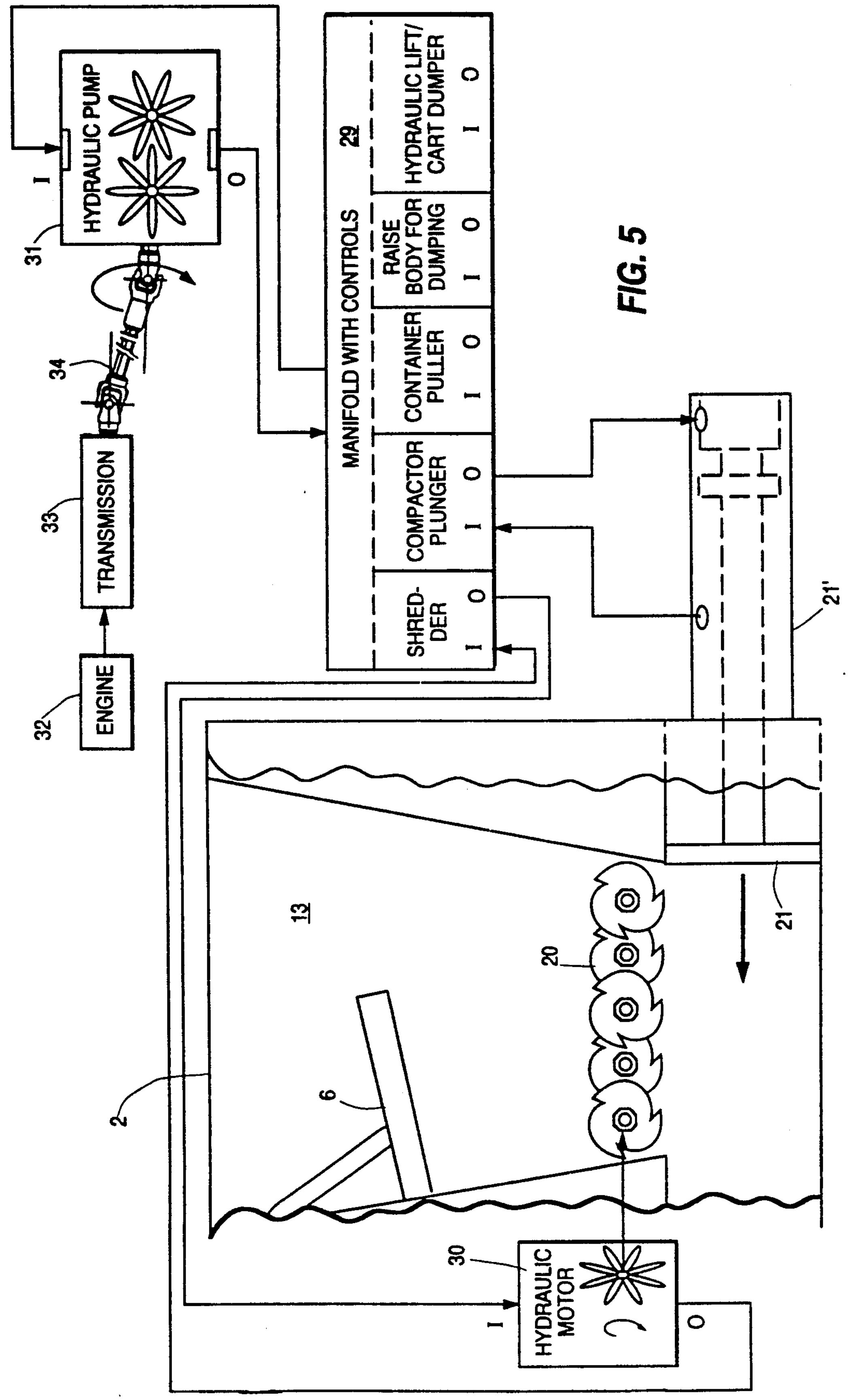
FIG. 5 is a schematic view of the control mechanism for operating the carrier.

Referring to FIGS. 2 and 3, a set of six control levers 22, 23, 24, 25, 26 and 27 are shown atop a control box 28 on the side of the truck. Referring now to FIGS. 4 and 5, the control box 28 houses a hydraulic manifold 29 which delivers hydraulic fluid to a hydraulic motor 30 for driving the shredder jaws 20. The hydraulic fluid for driving the hydraulic motor is obtained from a hydraulic pump 31 driven by the vehicle propulsion engine 32 (FIG. 5) through the vehicle transmission (33) which drives a vehicle propulsion shaft 34 from which power is taken to drive hydraulic pump 31. Lift piston 5 lifts rail 58 to fit under rollers 37 and cable 47, attached to storage area 2 and piston 51, extends and contracts against pulley 41 to draw storage area 2 on and off the chassis 4.

In addition to driving the hydraulic motor 30 which operates the shredder jaws 20, the hydraulic pump 31 also supplies hydraulic fluid under pressure to the compactor piston plunger 21, the receptacle dumping collar 17 and arm 18; the hydraulic lift piston 39 for raising container 2; the hydraulic lift cylinder 5; shredder bin cover 14 and anti-coning device 6. Each of the levers 22, 23, 24, 25, 26 and 27 are connected respectively to an input and output of the manifold for allowing hydraulic fluid to flow to the respective units designated.

Figure 8:
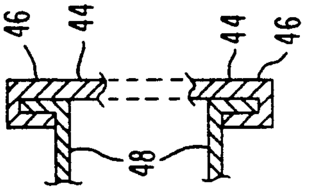
FIG. 8 is a sectional view of the channel track connection to the autoclave basket.

FIGS. 6, 7 and 8 shows the autoclave situated in a medical facility. The bagged medical waste at the facility is placed in waste basket 59 which is placed on platform 54 and raised by scissor arms 42 and 42$^1$ on scissor jack base 56 bolted by 52, under platform 54, to the autoclave housing level and pushed into autoclave 15 by operating gear 66 wherein the waste is sterilized. Basket 59 is shown with wheels 50 (FIG. 6). The scissor arms 42 are operated by cylinder 40 to raise and lower platform 54. The basket 59 is equipped with two "L" shaped tracks 48 which pivotably coact with a pair of "U" shaped tracks 46 (FIG. 8) coacting with basket guide rail to move basket 59 sufficient to engage gear 66, moving basket 59 in and out of autoclave 15. The basket 59 is pivoted on pin 45 of pivot assembly 44 to dump the autoclaved waste from opening 49 (FIG. 7), into a receiving receptacle 16, all driven by motor 35 on post 38 and 38$^1$ (FIG. 6 and 7). The motor 35 is operated from a control panel (not shown) in the medical facility. The waste pail 16 is set aside for processing in the shredder bin 13 as described heretofore.

Figure 9:
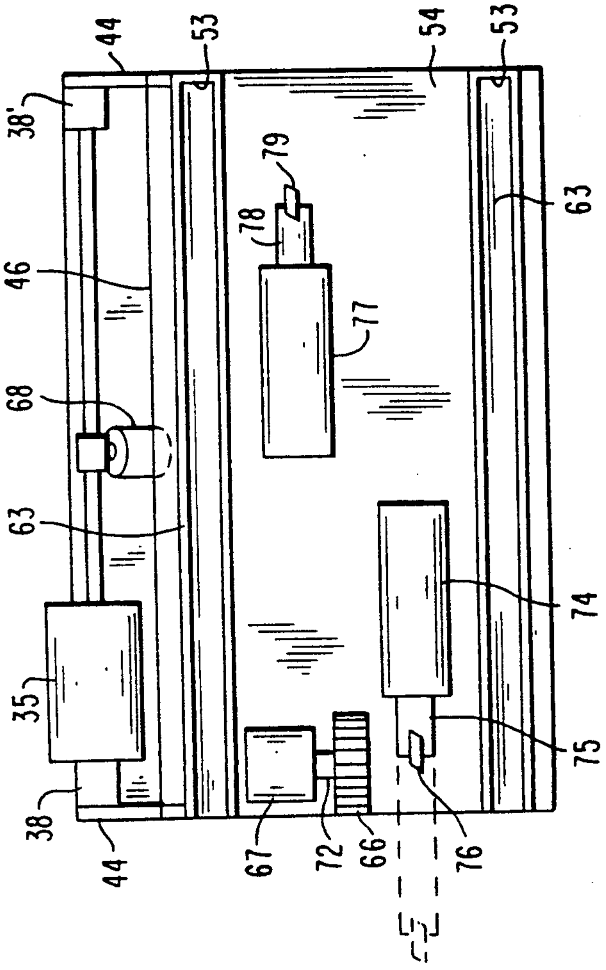
FIG. 9 is a top sectional view of the drive unit for removing the basket from the autoclave unit.

FIG. 9 shows how regulated medical waste is autoclaved by basket autoclaving. The waste is emptied into the open end 49 of basket 59 (FIG. 7), when scissor lift piston 62 is in the retracted position and scissor jack platform 54 in the load position. Cylinder 77 is actuated and piston 78 pulls basket 59 when latch 79 is activated to catch the basket 59 frame and the basket is positioned over the platform; basket gear 66 and the basket gear motor 67 is engaged pulling basket gear chain 65 (FIG. 7) into autoclave unit 15 on the receiving basket guide rails 43 (FIG. 6). The autoclave door is locked and the contents in the basket are sterilized by means which while not shown, are well-known in the art. After the sterilizing process is complete the autoclave door is opened, basket cylinder out 74 is activated and basket catch piston 75 extends into autoclave 15 and basket catch latch out control 76 engages at bottom of basket 59 which is wheeled out on wheels 50 along guide rail 63. The basket wheel guides 63 engage platform basket gear 66 to awaiting basket gear chain 65 (FIG. 7) and basket gear motor 67 continues to move basket 59 along rails 43 (FIG. 6) until basket wheels 50 reach basket stop 53 as basket 59 is moved onto scissor jack platform 54. "L" shaped basket track 48 slips into pivot assembly "U" track 46 (FIG. 8) attached to pivot assembly 44. Basket frame tilt cylinder 68 is engaged thus moving basket frame tilt piston 69 outward tilting pivot assembly 44 so that basket wheels 50 clear the opened door of the autoclave unit. Pivot assembly motor 35 is activated tilting pivot assembly 44 with basket 59 to empty contents of basket 59 into waiting receptacle 1 (FIG. 7). The filled receptacle can then be picked up and emptied into the truck-mounted shredder 20, shredded, compacted and stored on the truck ready for disposal.

It will thus be seen that the disposal of medical waste, infectious or otherwise, is reduced to operations involving a minimum of handling by personnel, and reduced to a form which can be readily disposed of at a sanitary landfill or waste disposal site after being mixed with other medical waste processed in like manner from other medical facilities, or even other solid waste including garbage.

Having thus described the invention, what is claimed is:

1. An autoclave for sterilizing medical waste comprising:

a) A housing having a bottom, side-walls and a top cover opening to receive bagged medical waste;

b) A basket adapted to fit and supported by the housing containing the bagged medical waste;

c) A platform in said housing for supporting the basket containing the bagged medical waste;

d) Means within the housing for sterilizing the bagged medical waste;

e) Means within the housing to move the platform upwardly and out of the housing with the basket of the sterilized medical waste thereon and to deposit the sterilized waste into a separate disposal container.

2. A steam autoclave as in claim 1 wherein the platform is lifted by scissor lift means and positioned for movement out of the autoclave.

3. A steam autoclave as claimed in claim 2 wherein the scissor lift means are a pair of scissor arms.

4. A steam autoclave as in claim 3 wherein the scissor lift means is a scissor or jack.

5. A steam autoclave as in claim 3 wherein the scissor means are driven by cylinder means to raise and lower the platform.

6. A steam autoclave as in claim 4 wherein the scissor means are driven by cylinder means to raise and lower the platform.

7. A steam autoclave as in claim 2 wherein the platform is pivotally mounted on rails to move the basket out of the autoclave and empty the same into the disposal container.

8. A steam autoclave as in claim 7 wherein the basket is pivoted by pin means driven by a motor within the autoclave unit.

9. A steam autoclave as defined in claim 8 wherein the motor is remotely operated.

* * * * *